United States Patent [19]
Cukjati

[11] Patent Number: 5,340,308
[45] Date of Patent: Aug. 23, 1994

[54] ADJUSTABLE DENTAL TRAY

[76] Inventor: Joseph F. Cukjati, 1916 Wendy St., Irving, Tex. 75060

[21] Appl. No.: 84,430

[22] Filed: Jun. 29, 1993

[51] Int. Cl.⁵ .......................... A61C 9/00; A61D 5/00
[52] U.S. Cl. ......................................... 433/41; 433/45; 433/1
[58] Field of Search ...................... 433/37, 41, 43, 45, 433/1

[56]  References Cited
U.S. PATENT DOCUMENTS

| 95,126 | 9/1869 | McDonald . | |
|---|---|---|---|
| 753,679 | 3/1904 | Davis . | |
| 1,054,999 | 3/1904 | Thein .................... | 433/41 |
| 1,486,039 | 12/1923 | Santos . | |
| 1,493,417 | 5/1924 | Arnett . | |
| 1,634,717 | 8/1925 | Light . | |
| 1,652,910 | 12/1927 | Psayla . | |
| 2,426,388 | 8/1947 | Chartrand .................... | 433/41 |
| 2,452,866 | 11/1948 | Oertel .................... | 433/41 |
| 2,722,744 | 11/1955 | Wagner . | |
| 3,890,711 | 6/1975 | Burns . | |
| 3,978,585 | 9/1976 | Holcomb .................... | 433/41 |

FOREIGN PATENT DOCUMENTS

| 3338401 | 5/1984 | Fed. Rep. of Germany ........ | 433/41 |
|---|---|---|---|
| 42483 | 7/1933 | France .................... | 433/41 |

Primary Examiner—Gene Mancene
Assistant Examiner—Cindy A. Cherichetti
Attorney, Agent, or Firm—Cox & Smith Incorporated

[57]  ABSTRACT

An apparatus and method for making either upper or lower dental impression of teeth for a mammalian patient by utilizing an impression tray having upstanding walls that are laterally and longitudinally adjustable. Those walls conform to the mouth of the patient but spaced from the exterior of the upper or lower teeth of the mammalian patient.

9 Claims, 6 Drawing Sheets

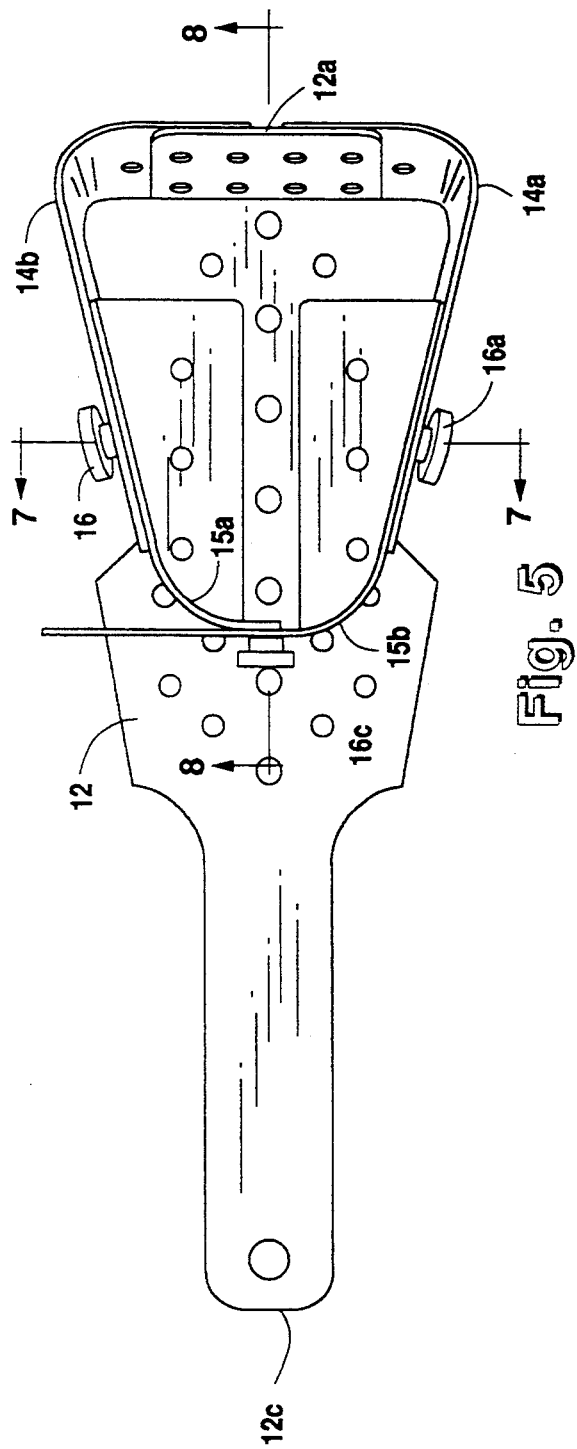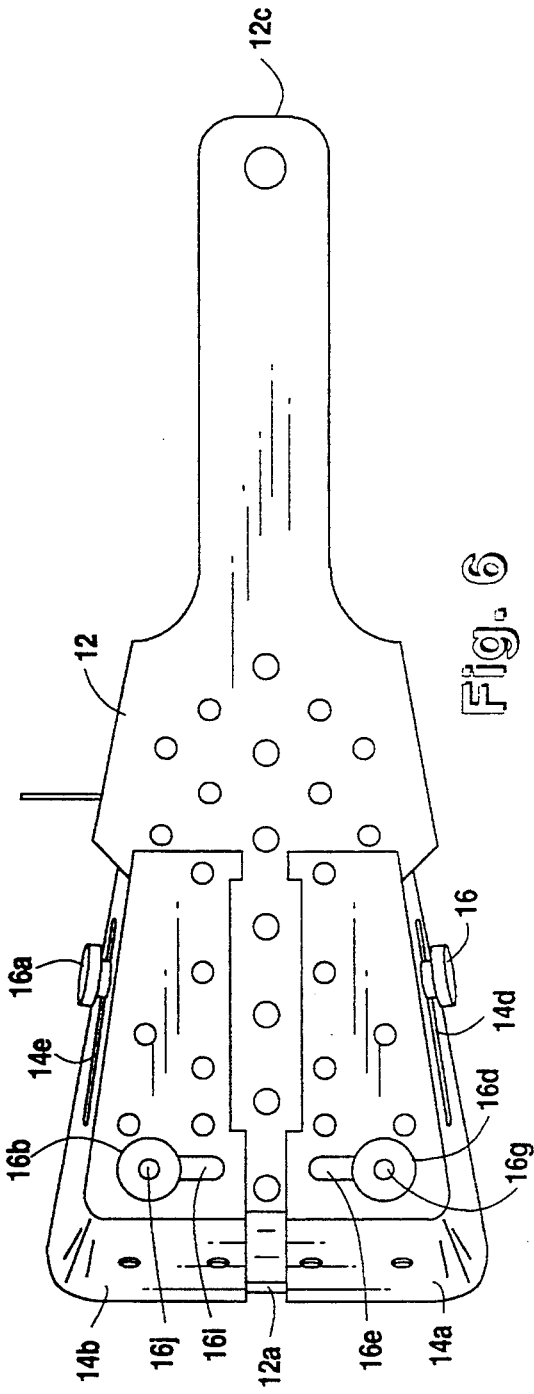

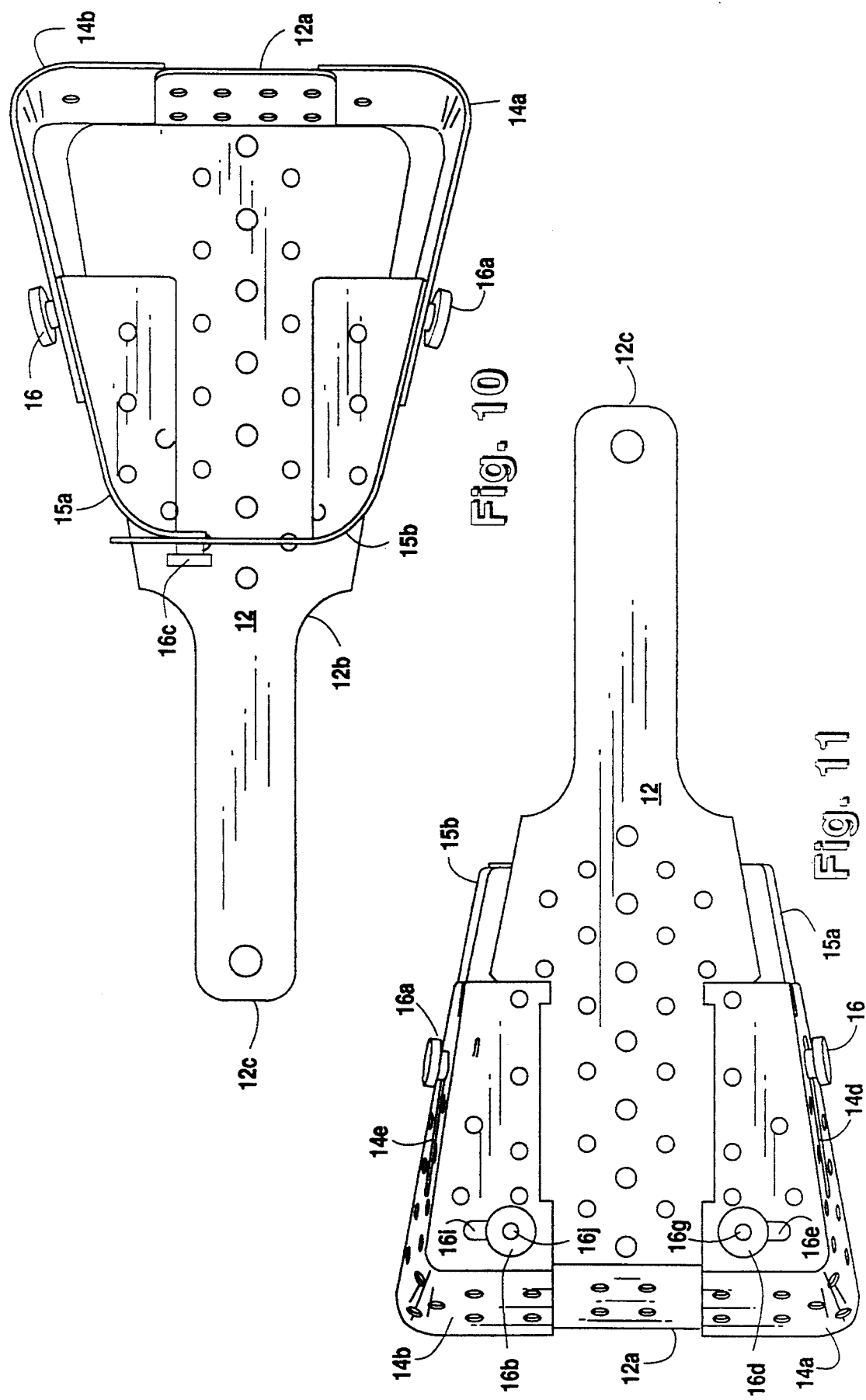

ADJUSTABLE DENTAL TRAY

FIELD OF THE INVENTION

The invention relates in general to a dental impression tray, in particular a dental tray used in applying impression paste around the teeth of a mammalian's mouth. In greater particularity, the invention relates to a dental tray that is adjustable to accommodate different sizes and shapes of dentition for canines and felines.

BACKGROUND OF THE INVENTION

Adjustable dental trays, in general, are well known in the art. An example of such a dental tray is U.S. Pat. No. 3,890,711 to Burns. Burns discloses an adjustable dental tray that has a primary unit and a complimentary unit slideably and telescopically mounted onto the primary unit for proximal and distal adjustments. The Burns patent satisfies the need for an adjustable positional tray in proximal and distal directions however, this invention does not allow for any lateral differences.

U.S. Pat. No. 2,722,744 to Wagner discloses a dental impression tray that has a pair of curved arms mounted onto the proximal end of the dental tray to allow for pivotal adjustments of the tray in an effort to account for various jaw sizes. The Wagner patent does not allow for any differences in sizes from the distal to the proximal end of the mammalian's mouth. Neither Burns nor Wagner provide for a varying degree of distal aspect in the distal retromolur area.

Accordingly, a need exists for an adjustable dental tray that can be adjusted to a wide variety of sizes to accommodate different sizes and shapes of dentition. Also needed is a dental tray that has a much deeper area on the proximal part of the tray to allow for a deeper bite into the impression material.

SUMMARY OF THE INVENTION

The invention is an adjustable dental impression tray that adjusts in the longitudinal and lateral directions allowing for various mammalian dentitions, but particularly for canines. The tray has a 30° distal aspect for holding the impression material in the tray and allowing more definity of the highly defined soft and hard tissue impressions of the distal retromolur area.

The present invention has a wider and longer range of tray adjustments, thereby, enabling the tray to conform to the various sizes and shapes of dentition. The adjustments of the tray allow for infinitesimal ranges of size extending to a length of about 5⅝ inch and extending in width to about 3¾ inch. The tray is randomly perforated with holes to allow a conventional semi-liquid dental impression material to pass through the holes thus securing the impression material in the tray when the semi-liquid material solidifies. The tray has a deeper area on the proximal end to allow a deeper bite into the impression material. Thus allowing for better definition of the total arch of the teeth and a complete impression of the soft tissues above the teeth.

The preferred embodiment of the present invention is an adjustable dental impression tray used in conjunction with impression material that is applied to the teeth of the mammalian's mouth. An example of impression material would be Alginate, a trade name for impression material commonly known as impression paste. In this particular embodiment, the dental impression tray has an elongated flat base having a distal end portion insertable in the mouth of the mammalian patient and a proximal end portion extending out of the mouth. A handle is formed on the proximal end portion suitable for grasping while making the dental impressions. A pair of forward paste retaining elements are respectively and adjustably secured to the distal portion of the bottom surface of the fiat base in anyone of a plurality of lateral spacings. A pair of rear paste retaining elements having their forward end portions respectively secured to the rear end portion of the forward paste retaining elements in any one of a plurality of longitudinal positions relative to the fiat base. The rear paste retaining elements have overlapping wall portions positionally adjacent to but exteriorly spaced from, the front teeth of the mammalian's mouth. The distal end portion of the flat base is bent upwardly to form a paste retaining barrier element to prevent the flow of the paste into the throat of the mammalian patient.

In second embodiment of the present invention, the flat base element and paste retaining elements are randomly perforated to permit flow of impression paste therein to solidify and prevent movement of the paste retaining elements during removal of the flat base element from the mammalian's mouth. In this embodiment of the present invention, the four retaining elements comprise a first pair of oppositely spaced L-shaped members laying on the top surface of the flat base element, a second pair of L-shaped members overlaying the bottom surface of the flat base element. The proximal ends of the first pair of L-shaped members have angularly bent upstanding walls disposed in overlapping relationship. The distal ends of the second pair of L-shaped members have angularly bent upstanding walls disposed in overlapping relation to the upwardly bent distal portion of the flat base element. Such upstanding walls form an adjustable width and length barrier around the perimeter of the flat base element.

The L-shaped members and upstanding walls are contoured to the mouth of a particular mammalian patient. This contour is provided by a 30° aspect of the upstanding wall portion of the L-shaped members. The L-shaped members along with their respective upstanding walls are adjustable, securable, and moveable in relationship to the flat base element. The mouth of the first pair of L-shaped members provide adjustment in the longitudinal direction and the second pair along with the first pair of L-shaped members provide for adjustment in the lateral direction.

The third embodiment of the present invention provides for a U-shaped insert element having at least one threaded stud attached to its bottom surface and that stud is insertable into mounting holes along the longitudinal center line of the proximal end portion of the base element. In this embodiment of the present invention another U-shaped element is mounted onto a substantially rectangular element, the U-shaped element extending upwardly relative to the rectangular element, the rectangular element having a plurality of spaced adjusting holes therethrough and adjustably secured to the distal portion of the flat base element. These inserts are attached to the flat base element to take impressions of individual teeth or small groups of teeth rather than impressions of the entire mouth. Using the special inserts conserves the use of expensive impression material by limiting that particular material to a small area of the flat base element containing the insert or inserts.

A method for making a dental impression using the adjustable dental tray requires some preliminary measurements be made of the longitudinal length and lateral width of the mammalian's mouth. After these measurements, the adjusting screws are made to slideably adjust the moveable sidewalls along the flat base portion of the tray. Loosening the adjusting screws thereby allows the upright side walls to freely move in relation to the flat base portion of the tray. The side walls of the proximal and distal end of the tray are laterally extended until the distal portion of the tray opens sufficiently to match the measured lateral width. The proximal portion of the tray adjacent to the handle is then extended until the total extension measured from the distal end of the tray to the proximal end of the tray equals the measured longitudinal length the mammalian's mouth. Tightening the adjusting screws thereby secures the tray with the measured lateral width and longitudinal length.

The final step is filling the tray with a semi-liquid dental impression material, inserting the tray, distal end leading, into the mammalian's mouth and then engaging the jaws of the mouth with the tray thereby forming a full dentition impression of the lower or upper teeth.

A complete appreciation for the invention and many of the advantages thereof will be readily perceived as the same becomes better understood by references to the following detailed description when considered in connection with the following drawings.

BRIEF DESCRIPTION OF THE DRAWINGS

FIG. 5 illustrates a top plan view of the adjustable dental tray in the fully closed position.

FIG. 6 illustrates a bottom plan view of the adjustable dental tray of FIG. 5.

FIG. 10 illustrates a top plan view of the adjustable dental tray in the fully open position.

FIG. 11 illustrates a bottom plan view of the adjustable dental tray of FIG. 10.

DETAILED DESCRIPTION

Figure 1:
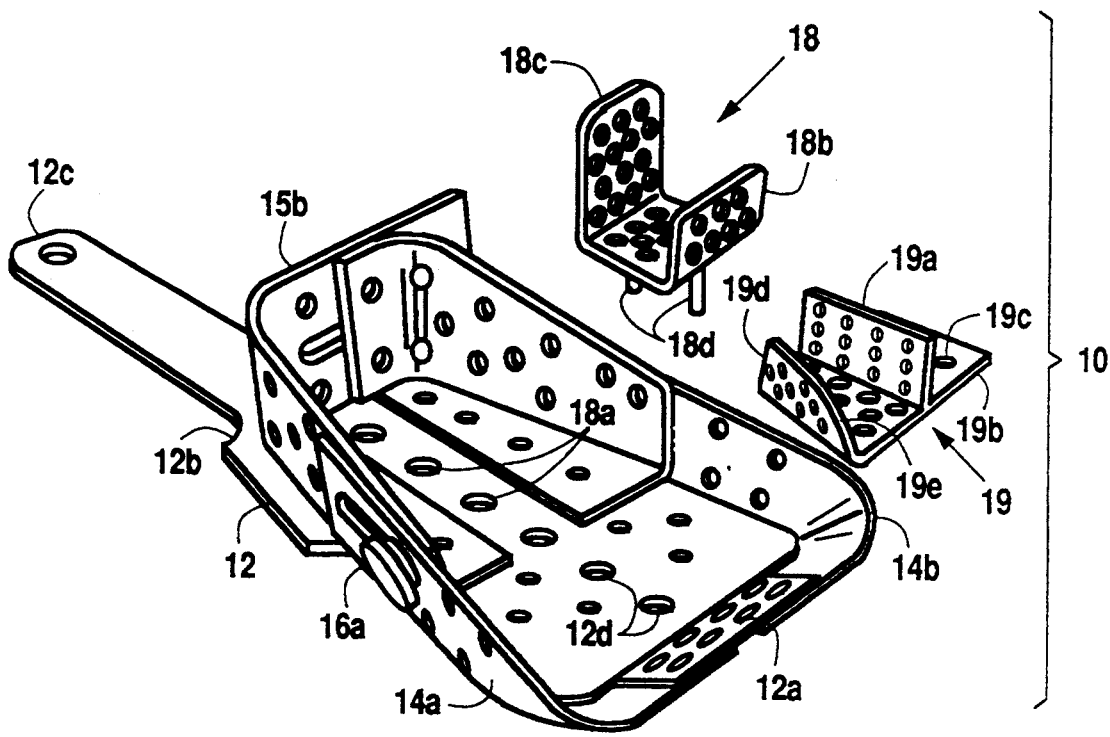
FIG. 1 illustrates an isometric top view of the adjustable dental tray in the distal extension and laterally closed position, with special inserts shown in exploded relation thereto.
Figure 2:
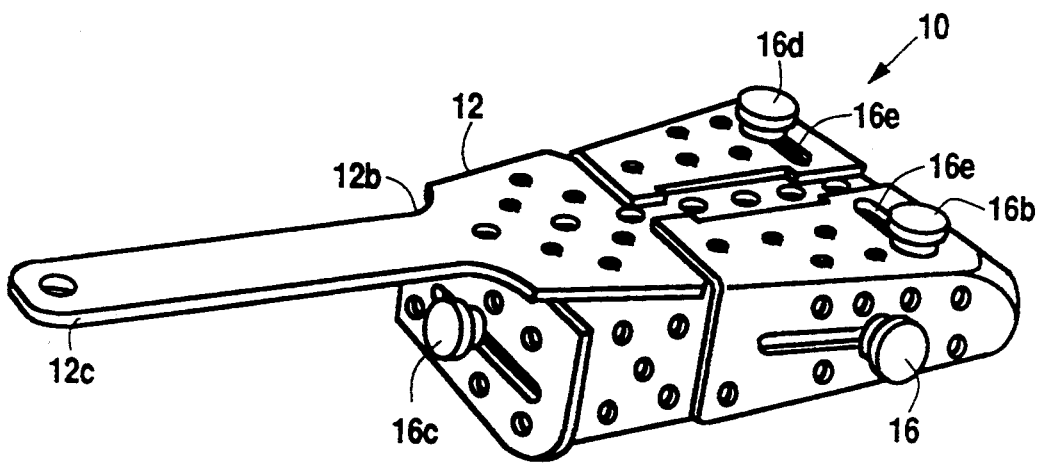
FIG. 2 illustrates an isometric bottom view of the adjustable dental tray of FIG. 1.
Figure 3:
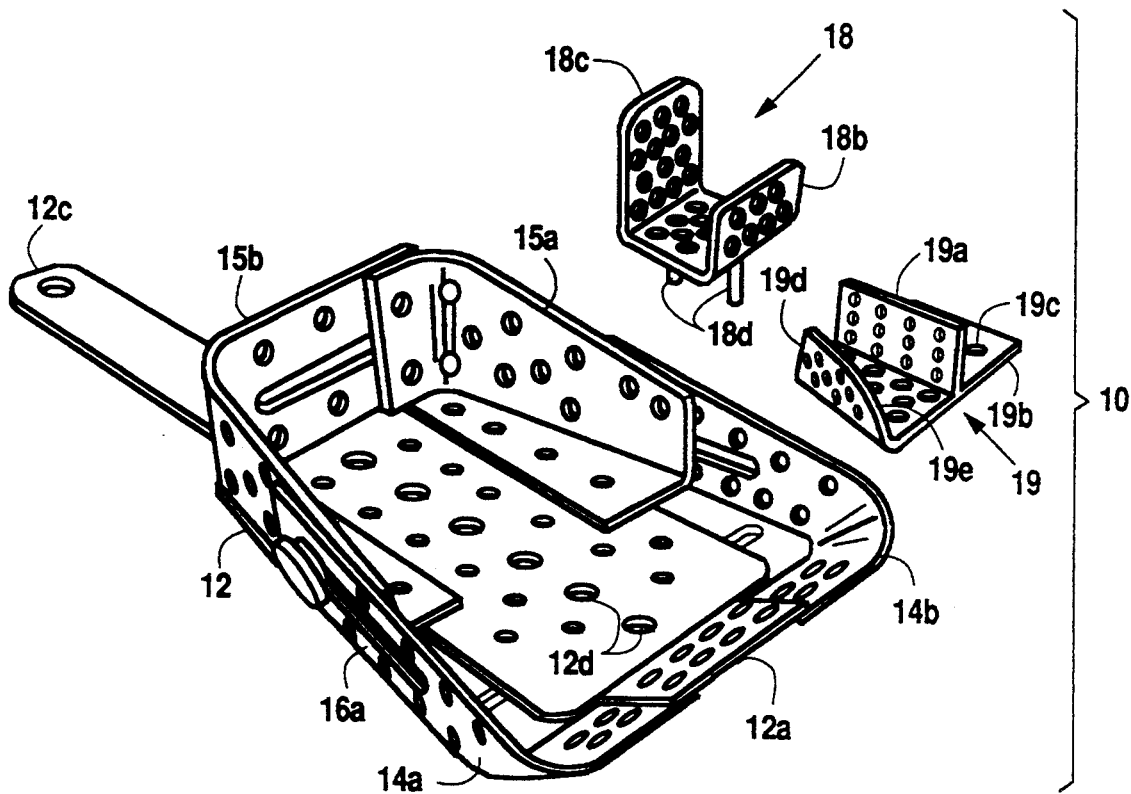
FIG. 3 illustrates an isometric top view of the adjustable dental tray in the distal extension and laterally open position.
Figure 4:
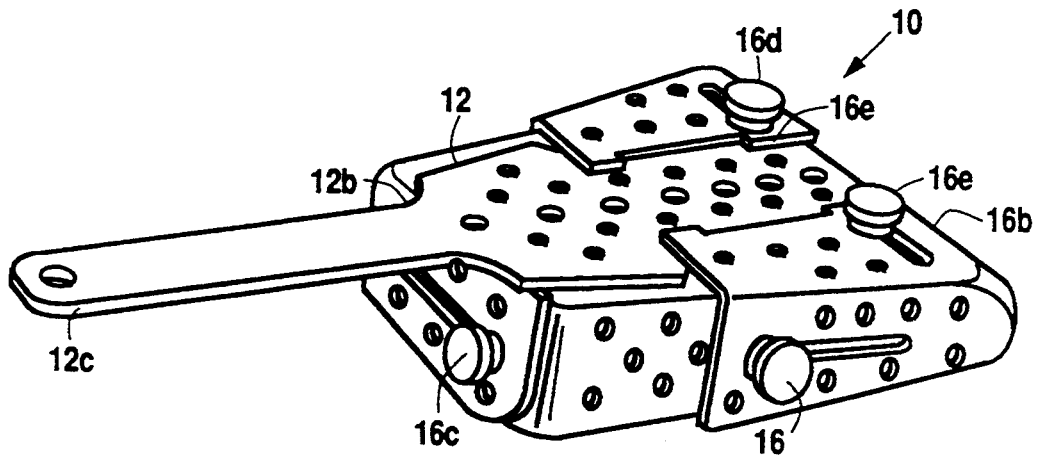
FIG. 4 illustrates an isometric bottom view of the adjustable dental tray of FIG. 3.
Figure 8:
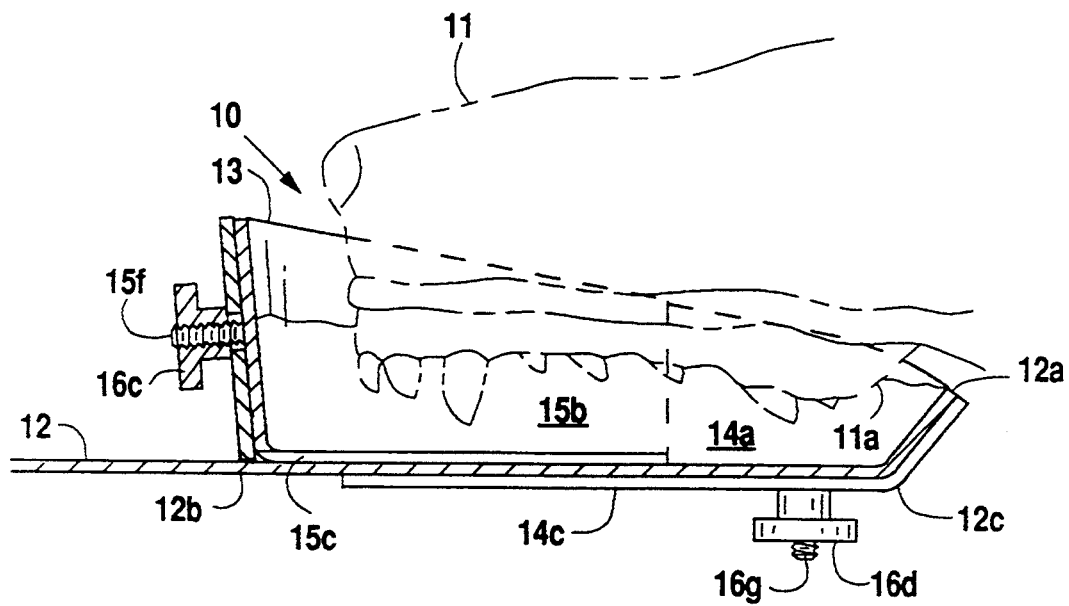
FIG. 8 illustrates an environmental vertical cross-sectional view of the adjustable dental tray as applied to a canine's mouth.
Figure 9:
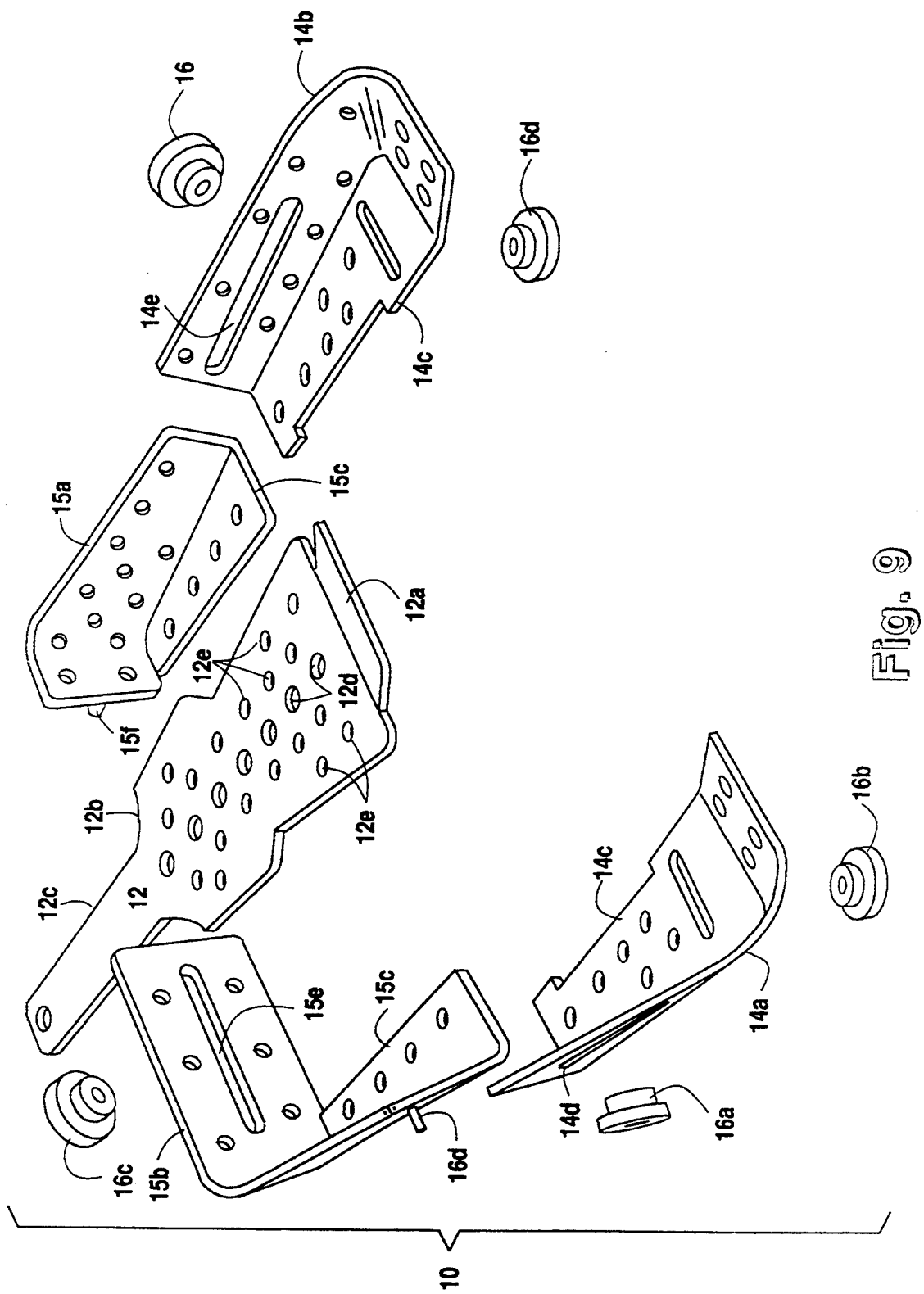
FIG. 9 illustrates an exploded isometric view of the adjustable dental tray.

The preferred embodiment of the present invention is illustrated generally at 10 of FIG. 9. An elongated flat base element 12 has a distal end portion 12a that is insertable into the mouth of a mammalian patient and a proximal end portion 12b extending out of the mouth of the mammalian patient. A handle 12c suitable for grasping is formed on the proximal end portion 12b. L-shaped base members 14a and 14b have their respective base portions 14c configured to abut the distal bottom surface of flat base element 12 as shown in FIG. 2. L-shaped base members 15a and 15b, have their respective base portions 15c configured to abut the proximal top surface of flat base elements 12 as shown in FIG. 1. The L-shaped members 14a, 14b, 15a, and 15b are configured to form upstanding sidewalls around flat base element 12's distal end portion 12a and proximal end portion 12b, as shown in FIGS. 1 and 2. The upstanding walls also form a 30° distal aspect 13 (FIG. 8), that distal aspect 13 provides a deeper dention of the retromolur area of the mammalian patient.

An environmental view of the dental tray 10 inserted into the mouth of the mammalian patient is illustrated in FIG. 8. In this embodiment, the patient is a dog 11 having a dental impression made of it's upper teeth. FIG. 8 shows the relative position of dental tray 10 in relation to dog 11, i.e., the side walls are adjacent to but exteriorly spaced from the front teeth of dog 11. FIG. 8 also illustrates distal aspect 13 providing the deep dentition of the retromolur area 11a of dog 11. In addition, FIG. 8 illustrates base portion 14c abutting the bottom distal end portion 12a of base 12 and base portion 15c abutting the top proximal end portions 12b of flat base element 12.

Figure 7:
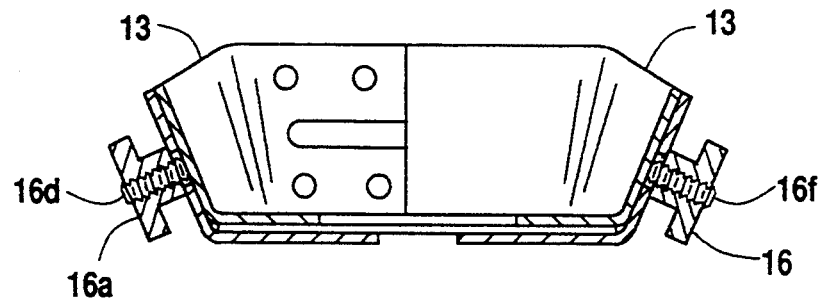
FIG. 7 illustrates a sectional view of a proximal portion of the adjustable dental tray taken on the plane '7-7 of FIG. 5.

When L-shaped members 14a and 15b are assembled onto flat base element 12 in a abutting overlaying relationship, threaded extension stud 16d (FIG. 9) laterally projects through slot 14d of L-shaped member 14a (FIG. 9). FIG. 7 illustrates stud 16d projecting through slot 14d and lateral adjustment knob 16a securely fastening L-shaped members 14a to 15b. Also, when L-shaped members 14b and 15a are assembled onto flat base element 12 in an abutting overlaying relationship, threaded extension stud 16h (FIG. 7) laterally projects through slot 14e (FIG. 9) of L-shaped member 14b (FIG. 7). Lateral adjustment knob 16 (FIG. 7) securely fastens L-shaped members 15a and 14b. Slots 14d and 14e have extension guides for the L-shaped members 15a and 15b to telescopically move along the longitudinal length of the proximal end 12b of flat base element 12. L-shaped members 15a and 15b are secured in any one of various positions along the longitudinal length of flat base element 12 by securely adjusting knobs 16 and 16a that engage extension studs 16d and 16h.

Flat base element 12 has two downwardly projecting threaded studs 16g (FIG. 6) and 16j (FIG. 6). These studs project through slots 16e and 16i (FIG. 6) when L-shaped members 14a and 14b are assembled onto flat base element 12. These slots 16e and 16i provide guidance for thread studs 16g and 16j, respectively; as the L-shaped members 14a and 14b are extended in the lateral direction providing for various lateral widths of the mammalian patient's mouth. FIG. 8 illustrates the relationship between the patient's mouth, in this case the patient is dog 11, and L-shaped members 14a and 15b. These two members 14a and 15b as well as L-shaped members 14b and 15a (not shown in FIG. 8) are parallel to and externally positioned from dog 11 teeth and mouth. FIGS. 5 and 6 illustrate dental tray 10 in the fully closed position and FIGS. 10 and 11 illustrate dental tray 10 in the fully open position. Dental tray 10 may be adjusted to any position between fully open and fully closed to accommodate various mouth sizes of mammalian patients.

The proximal end portion of L-shaped member 15b has a lateral extension adjusting slot 15e. Threaded stud 15e (FIG. 8) extends through slot 15c when L-shaped members 15a and 15b are assembled onto flat base element 12. Lateral extension slot 15c provides guidance to thread stud 15f when L-shaped members 15a and 15b are being laterally adjusted. Adjusting knob 16c secures the proximal lateral positioning of L-shaped numbers 15b, 15a, 14a, and 14b when these elements are laterally spaced to accommodate various mouth sizes.

The procedure for adjusting dental tray 10 to the fully open position, as illustrated in FIGS. 10 and 11, requires lateral adjust knobs 16b, 16c, and 16d to be loosened from their fully secured position on their respective threaded studs 16h, 15e, and 16g. The two pairs of L-shaped members 14a, 15b, 14b and 15a are free to moved in a lateral relationship with base element 12. The two pairs of L-shaped members 14a, 14b and 15a, 15b are extended laterally until threaded studs 16h and 16g rest against the end portion of slot 16e and 16i, as shown in FIG. 11, thereby fully extending dental tray 10 to its maximum width. The maximum length of dental tray 10 is provided for by loosening adjusting knob 16 and 16a from the respective threaded studs 16d and 16h. Then extending L-shaped members 15a and 15b along the longitudinal length of the proximal portion of dental tray 10 until studs 16h and 16d rest against the end portions of slot 14e and 14d as illustrated in FIGS. 10 and 11.

FIGS. 5 and 6 illustrate the two pairs of L-shaped members 14a, 14b and 15a, 15b in the fully closed position in relation to the flat base element 12. This fully closed position is only one extreme of the many secured positions dental tray 10 can be adjusted to when adjusting knobs 16a, 16 and 16c are loosened from their respective studs 16d, 16e, and 16h.

The fully open or fully closed position illustrated in FIGS. 10 and 11 or FIGS. 5 and 6 show only one of the many positional locations for L-shaped members 14a, 14b, 15a and 15b in relation to flat base element 12.

In this embodiment of the present invention specialized dental impression of individual or small groups of teeth can be made by using a substantially U-shaped element 18 (FIG. 1). U-shaped element 18 has a lower distal portion 18b in relation to proximal portion 18c. Proximal portion 18c is perforated with a plurality of holes to provide a retaining barrier for dental paste when impressions are made. The bottom portion of U-shaped element 18 has two downwardly projecting threaded studs 18d that may be inserted into holes 12d along the longitudinal length of flat base element 12. These mounting holes provide the necessary adjustment positioning for U-shaped insert 18.

FIG. 1 also illustrates a second insert element 19 mounted to a substantially rectangular base 19b. Base 19b has a plurality of mounting holes 19c for positioning insert element 19 in anyone of the plurality of holes found in flat base element 12. Insert element 19 has an upstanding wall 19a that provides one side of the necessary retaining wall when the user is making a dental impression of only an individual tooth or small group's of teeth. Insert element 19 has a second upstanding wall 19d. Wall 19d has a curved position 19e to accommodate the distal aspect at the molar region of the patient's mouth much the same way as distal aspect 13 (FIG. 8) contours to the full distal aspect of the patient's mouth. Insert elements 18 and 19 are used when it is desired to make dental impressions of individual or small groups of teeth.

The invention now being fully described, it will be apparent to one of ordinary skill in the art that many changes and modifications can be made thereto without departing from the spirit or scope of the invention as set forth herein.

I claim:

1. An adjustable dental impression tray for applying an impression paste around the teeth of mammalian mouth, comprising, in combination:
   an elongated flat base element having a distal end portion insertable into the mouth of the mammalian and a proximal end portion extending out of the mouth;
   a handle formed on said proximal end portion;
   said flat base element having a flat top surface and a flat bottom surface;
   a pair of forward paste retaining elements respectively secured to the distal portions of said flat bottom surface in any selected one of a plurality of lateral spacings;
   a pair of rear paste retaining elements having forward end portions respectively secured to the rear end portions of said forward retaining elements in any selected one of a plurality of longitudinal positions relative to said base plate;
   said rear paste retaining elements having overlapping wall portions positionably adjacent to but exteriorly spaced from, the front teeth of the mammalian's mouth; and
   said distal end of said flat base plate being angularly bent upwardly to abbutingly engage the distal end of said forward paste retaining elements forming a paste retaining barrier element to the flow of said paste into the mammalian's throat.

2. An adjustable dental impression tray as recited in claim 1, wherein said base element and said paste retaining elements are randomly perforated to permit flow of impression paste therein to solidify and prevent movement of said paste retaining elements during removal from the mammalian's mouth.

3. An adjustable dental impression tray as recited in claim 1, wherein said forward retaining elements comprise a pair of L shaped members overlaying said bottom surface of said flat base element, said L shaped members each having an upstanding wall attached thereto and contoured to lie parallel to exterior of the gums of the mammalian's mouth.

4. An adjustable dental impression tray as recited in claim 3, wherein said contour of said upstanding walls extends from the incisor region to the molar region of the mammalian's mouth.

5. An adjustable dental impression tray as recited in claim 1 wherein said rear retaining elements comprise a pair of L shaped members overlaying said top surface of said flat base member, said L shaped members each having an upstanding wall attached thereto and contoured to lie parallel to the mouth of the mammalian's mouth.

6. An adjustable dental impression tray as recited in claim 5, wherein said contour of said upstanding walls extends from the incisor region to the molar region of the mammalian's mouth.

7. An adjustable dental impression tray as recited in claim 5 wherein said upstanding walls each having an outwardly projecting threaded stud; and
   said stud cooperating with a tightening knob to adjustably secure said rear paste retaining elements to said forward paste retaining elements.

8. An adjustable dental impression tray as recited in claim 1 further comprising an U shaped insert tray having at least one thread stud attached to the bottom surface of said insert tray, said tray being mounted along the longitudinal center line of said proximal end portion.

9. An adjustable dental impression tray as recited in claim 1 further comprising an U shaped insert element having a flat base and sidewalls extending upwardly therefrom;

a substantially flat rectangular element having mounted thereon said insert element;

said rectangular element having a plurality of spaced adjusting holes therethrough; and said rectangular element being adjustably secured to said flat base element's distal portion.

* * * * *